(12) United States Patent
Pacheco, Sr.

(10) Patent No.: US 6,683,228 B1
(45) Date of Patent: Jan. 27, 2004

(54) LUMINOUS TELE-DIAPER

(76) Inventor: Angel Luis Pacheco, Sr., 1221 Pinetree Dr., Melbourne, FL (US) 32937

( * ) Notice: Subject to any disclaimer, the term of this patent is extended or adjusted under 35 U.S.C. 154(b) by 0 days.

(21) Appl. No.: 09/575,741

(22) Filed: May 22, 2000

Related U.S. Application Data

(63) Continuation-in-part of application No. 09/241,799, filed on Feb. 2, 1999.

(51) Int. Cl.[7] ................................................. A61F 13/15
(52) U.S. Cl. ....................................................... 604/361
(58) Field of Search .......................................... 604/361

(56) References Cited

U.S. PATENT DOCUMENTS

| | | | | |
|---|---|---|---|---|
| 3,738,299 A | * | 6/1973 | Packler et al. ............... | 112/439 |
| 4,244,369 A | * | 1/1981 | McAvinn et al. ............ | 604/362 |
| 5,389,093 A | * | 2/1995 | Howell ........................ | 604/361 |
| 5,435,010 A | * | 7/1995 | May ............................. | 2/67 |

* cited by examiner

Primary Examiner—Weilun Lo
Assistant Examiner—Catharine L. Anderson
(74) Attorney, Agent, or Firm—Prose

(57) ABSTRACT

A luminous phosphorescent color monitoring system build into or added to a cloth or disposable absorbent diaper or any personal hygiene utensil to confirm the state of the apparatus. The functioning bright color indicating system is also detectable in the dark and develops when body secretions are effecting the apparatus and the built in system registers the interface of the natural human secretions which catalyst and develops the positive visual format on the outer stratified layer of the utensil. The functioning pigments are water compatible, non toxic or detrimental to humans and calls for the observance of a bright luminous color emitted mostly in the inner surface of the outer layer of a diaper liner or commercially available pamper. The same format is applicable for other applications and the delivery of medications includes burn victims and oozing that should be closely monitored after a wound or surgery and the inclusion of a large diaper or oversize gauze pad or special body suit used for medications delivery systems when treated with the luminous substance and medications. Therefore it is no longer necessary to prove or pry open a diaper for verification nor oppose the new theory of visual monitoring for verification. This new and advantageous visual technology may now be developed for many other uses due to its natural and unsophisticated applicability and adaptations which includes industrial manufacturing procedures and the unpredictable oxygen or fuel leak detection.

20 Claims, No Drawings

LUMINOUS TELE-DIAPER

CROSS REFERENCES TO RELATED APPLICATION

This is a continuation-in-part of U.S. patent application Ser. No. 09/241,799 having a filing date of Feb. 2, 1999, titled "Tele-Diaper".

BACKGROUND OF THE INVENTION

Field of the Invention

This invention relates generally to the field of personal hygiene, and more particularly to a luminous, phosphorescence color status monitoring system that is also identifiable in the dark. Generally described and in comparison to existing documents, the patent awarded to inventor Baker, et al., U.S. Pat. No. 3,675,654 on Jul. 11, 1972 depends on permeation, excreted matters and the use of talc which are the main ingredients required for the verification system. Again the patent issued to Roe, et al., U.S. Pat. No. 5,569,232 on Oct. 29, 1996 contains a system where a color verification method is integrated into pampers for the purpose of making possible visual verification of the apparatus status.

SUMMARY OF THE INVENTION

The primary advantage of the present invention is to make easier the visual monitoring of sanitary conditions before they progress into a critical stage and to take complete advantage of the new visual identification method.

Another object of this invention is to provide an earlier warning system to motivate caregivers into prompt action.

It is yet another object of this invention to associate this technology to other areas where visual monitoring is essential during nontoxic enclosed manufacturing procedures and pinpointing of problem areas is of most importance.

It is yet another object of this invention to make possible the spontaneous identification of any part of the human body dysfunctional areas with pin point accuracy on the first attempt and prevent the usage of other chemicals that might not be human flesh compatible.

It is yet another object of this invention to maintain alertness by visually monitoring topical problems on a human torso as well as that of other mammals and in the process associate this new technology to already established new science applications known as cold light applications like phosphorescence which is the emission of light without combustion or perceptible heat, chemiluminescence commonly known for the emission of light by certain chemical reactions which is commercially available for many other uses, bioluminescence the giving of light by means other than heat and of living things, photochemistry the branch of chemistry that deals with technical action of light with photoluminescence pigments and the daylight fluorescent pigments which are commonly know as none toxic pigments.

Human beings as well as all other organism must have phosphorous to live and it is induced into their metabolism from the plants and animals they consume. Once both animals and plants die, certain bacteria breaks the dead organic matter and returns phosphorous to the soil where it may get recycle many times before it is washed to sea and is trapped as marine sediment.

This invention consists of a simple chemical technology which is noticeable for its constant presence in the market place and by the many article in use in our homes, work place and daily association to advanced gadgetry in our society. The new interfacing and use will elevate the technology into a higher level and make color verification more amicable and easier to understand. It will also be more noticeable and the response should be faster to correct the nature of a situation that if not taken care of immediately could lead into a complicated health matter. This new technological breakthrough is aided by the new luminous phosphorescence color status monitoring system that also has more diverse applications and adaptations.

The system is in the form of additives that when formulated will develop into a phosphorescent glow which is also identifiable in the dark. As in the past, permeation of the protection vehicle from any human needs like urination, defecation, sweating, bleeding, oozing or any other form of exuded action of the body becomes the catalyst or trigger mechanism for the system to take effect and develop to its total extent due to the fact that all the chemicals used are reactant to acid like ammonia in excreta.

The association with the latest technologies now available from many different sources will help in the enhancement of this invention to newer and more sophisticated applications whereby a more concrete product dependency may be established. The manufacturing of any of the by products of this technology will be of a moderate and affordable price to the consumer and will not require an expensive retrofit of our existing manufacturing process or industry and it will also fit into the most modest, accelerated or prestigious and aggressive marketing atmosphere of all nations.

The era of probing is now superseded along with the sense of smell for the analysis of a common human function and now the consumer will benefit from a product that is not only user friendly but a staple that is programmed to return our loved ones that are dependent on others for their care, to a fast and dignified status. The transition to the new technology will be a spontaneous reaction and there will be no formal training to get acquainted with the system.

This is a system that may be stored indoors or displayed at any retail facility without fire danger restrictions, it is home safe, luggage safe, air and surface transportable as a part of a family travelling kit, ambulance, train, ships, aircraft, field training detachments and other activities. This new technology has also added a new ingredient to the old article called diaper or breechcloth as well as patented utensils that will take them into a higher dimension in the new millenium because there is simply no need to prove, pry or peep into the front or back of the vehicle to establish the need for physical hygiene maintenance.

The new system is a formidable candidate for inclusion into hospital surgery rooms as well as all other areas as a new tool for the detection and care of other forms of secretions experimentation or simulation that includes training or wounds oozing or the care of large burn areas that may be covered with a large diaper, pamper, a new large sterile clinical garment with zippers or velcro capable of encasing a child or adult body for burn treatment made of paper, fabric or plastic treated with the luminous compound plus whatever other medication requires delivery as part of a treatment like zinc oxide known as $Z_nO$ used in the treatment of some skin conditions.

DETAILED DESCRIPTION OF THE INVENTION

The present new invention is provided with a luminous phosphorescent color status monitoring system capable of maintaining vigilance during day light hours as well as night time or during darkness. The system in its totality is an early warning system made from common ingredients known as magnesium silicate and talc known as $H_2Mg_3(S_1O_3)_4$ which is typical in the production of baby powders and lubricants. The talc will be supported by the addition of natural phosphoric acid known as $H_3PO_3$ for the luminescence reaction.

Starch may now be added to the process as a new form of powder made from corn, a natural food product known as $(C_8H_{10}O_5)N$ and tricalcium phosphate $C_3(PO_4)_2$ The next agent added to the process will be the phosphorous $H_3PO_3$ to complete the mix that will be accelerated during excretion and the introduction of the natural acid contained in the excreted human waste in the form of ammonia which will be the trigger mechanism to develop or make a luminiferous occurrence a printed positive.

The commercially available disposable diapers are manufactured in a xerophyte type of assembly which makes them excellent for upgrading with a phosphorated system of phosphorous and the other agents required for a total conversion. The agents and chemicals may be in a powder form, a jell, a wax, a paste or any crystallized format accompany by their respective chemical binder. The xerophilous nature of talc or starch will be very useful and economical in it's natural state blended with luminous phosphorous as a sprinkle agent to augment cloth diapers and to phosphorate the more exotic pampers.

The chemical agents may be located within the stratified assembly or strategically placed in vital areas where saturation or permeation are more likely to occur. The inner side of the outer layer would be the most logical location because the clear outer ply will be the outer protective see through training pant.

The luminous phosphorescent status monitoring system is of a simple nature and the developing to its final luminous stage will materialized when normal human excreted matters such as urine and feces are introduced into a cloth diaper, commercially available disposable diapers, or any other personal hygiene utensil such as a sanitary napkin, breast pads, under arm pad, surgical drain pad, also special oversize sterile gauze pad with see through bar type window and padded tape strips of the new luminous phosphorated type.

The luminous property applied to the implement may be in powder form, jell, wax, paste or any crystallized format however any humectant interface will commence the transition modulation relative to the reactant of substances to effect the positive print of the luminous phosphorescent creation regardless of the quality of the substance xerophyte or gelatinoid state affixed to the stratified assembly of any personal hygiene implement. The substance may be applied within the stratified assembly or directly on the inside of the outer layer of a diaper that is protected by a translucent protector or outer plastic pants.

The application of the options are numerous like a printed outline design of an actual flow circuit which will be imprinted on the inner side of the outer layer to direct any fluid discharges toward a specific path treated with the applicable chemicals that once contacted will develop into the luminous pattern. The circuit pattern would be designed for this explanation around the lower human body lower extremities and to conform to the specific suspected areas of possible leakage.

The luminous compound of the phosphorous ($H_3PO_3$) is typically used as a chemical reducing agent and may be applied to the garments by sprinkling, rubbing, brushing, spraying, compressed air spray cans, hand pumped mist sprayer or other means or methods or it can be built into diapers or disposable absorbent pampers. The luminous phosphorescent properties will also be advantageous in other technologies, like leak detection in wood, metal, plastic, masonry and others where restrictions and environmental control laws are imposed and dictate the kind and type of agent allowed in the immediate work area where only explosion proof portable black lights for inspections are allowed.

It is to be understood, however, that even though numerous characteristics and advantages of the present invention have been set forth in the foregoing description, together with details of the structure and function of the invention, the disclosure is illustrative only, and changes may be made in detail, especially in matters of formulas, colors, compounds, shape, size, and arrangement of parts within the principles of the invention to the full extent indicated by the broad general meaning of the terms in which the appended claims are expressed.

What I claim as my invention is:

1. A diaper for detecting human excretions including ammonia, said diaper comprising:

a body having a surface for receiving human excretions therein; and an illuminable element applied to the surface of said body and for determining the presence of human excretions including ammonia, said illuminable element including magnesium silicate, phosphorous and starch, said illuminable element reacting with ammonia in human excretions and thereby causing said body to illuminate for visibly identifying a portion of said diaper that has contacted human excretions.

2. The diaper of claim 1, wherein said body is formed from disposable material.

3. The diaper of claim 1, wherein said body is formed from cloth.

4. The diaper of claim 1, wherein said body is formed from synthetic material.

5. The diaper of claim 1, wherein said body further comprises a stratified portion, said illuminable element contacting said stratified portion.

6. The diaper of claim 1, wherein said body is formed to be generally soft.

7. The diaper of claim 1, further comprising a transparent layer connected to said body.

8. An apparatus for detecting human excretions including ammonia, said apparatus comprising:

a body for receiving human excretions therein and including a first layer formed from disposable material; and an illuminable element applied to said first layer and for determining the presence of human excretions including ammonia, said illuminable element including magnesium silicate, phosphorous and starch, said illuminable element reacting with ammonia in human excretions and thereby causing said first layer to illuminate for visibly identifying whether said apparatus has contacted human excretions.

9. The apparatus of claim 8, wherein said disposable material comprises cloth material.

10. The apparatus of claim 8, wherein said body is formed from synthetic material.

11. The apparatus of claim 8, wherein said body further comprises a stratified portion, said illuminable element contacting said stratified portion.

12. The apparatus of claim 8, wherein said body is formed to be generally soft.

13. The apparatus of claim 8, further comprising a transparent layer connected to said body.

14. The apparatus of claim 13, wherein said body further includes an outer surface, said transparent layer being connected to said outer surface.

15. A diaper for detecting human excretions including ammonia, said diaper comprising:
- a body for receiving human excretions therein and including a first layer formed from disposable material including cloth material; and
- an illuminable element applied to said first layer and for determining the presence of human excretions including ammonia, said illuminable element including magnesium silicate, phosphorous and starch, said illuminable element reacting with ammonia in human excretions and thereby causing said first layer to illuminate for visibly identifying whether said diaper has contacted human excretions.

16. The diaper of claim 15, wherein said body is formed from synthetic material.

17. The diaper of claim 15, wherein said body further comprises a stratified portion, said illuminable element contacting said stratified portion.

18. The diaper of claim 15, wherein said body is formed to be generally soft.

19. The diaper of claim 15, further comprising a transparent layer connected to said body.

20. The diaper of claim 19, wherein said body further includes an outer surface, said transparent layer being connected to said outer surface.

* * * * *